(12) United States Patent
Korpela

(10) Patent No.: US 6,468,810 B1
(45) Date of Patent: Oct. 22, 2002

(54) MAGNETIC PARTICLE TRANSFER DEVICE AND METHOD

(75) Inventor: Matti Korpela, Naantali (FI)

(73) Assignee: Bio-Nobile Oy, Turku (FI)

( * ) Notice: Subject to any disclaimer, the term of this patent is extended or adjusted under 35 U.S.C. 154(b) by 0 days.

(21) Appl. No.: 09/600,816

(22) PCT Filed: Feb. 19, 1999

(86) PCT No.: PCT/FI99/00135
§ 371 (c)(1),
(2), (4) Date: Jul. 24, 2000

(87) PCT Pub. No.: WO99/42832
PCT Pub. Date: Aug. 26, 1999

(30) Foreign Application Priority Data

Feb. 23, 1998 (FI) .................................................. 980399

(51) Int. Cl.⁷ ............................................. G01N 33/553
(52) U.S. Cl. ......................... 436/526; 422/50; 422/98; 422/63; 422/64; 422/99; 422/100; 422/101; 422/104; 210/695; 210/22; 210/416.1; 210/224; 210/232; 435/287.1; 435/288.6; 435/288.4
(58) Field of Search ............................ 422/50, 98, 63, 422/64, 99, 100, 101, 102, 104; 210/695, 22, 416.1, 224, 232; 436/526; 435/287.1, 288.6, 288.4

(56) References Cited

U.S. PATENT DOCUMENTS

| | | | |
|---|---|---|---|
| 4,067,810 A | | 1/1978 | Sullivan ...................... 210/223 |
| 4,649,116 A | * | 3/1987 | Daty et al. .................. 435/287 |
| 4,751,053 A | * | 6/1988 | Dodin et al. ................. 422/101 |
| 4,855,045 A | * | 8/1989 | Reed ........................... 210/223 |
| 5,647,994 A | * | 7/1997 | Tuunanen et al. ........... 210/695 |
| 5,695,165 A | * | 12/1997 | Moriarty .................. 248/316.8 |
| 5,736,033 A | * | 4/1998 | Coleman et al. ............. 210/122 |
| 5,837,144 A | | 11/1998 | Bienhaus et al. ............ 210/695 |
| 6,065,605 A | * | 5/2000 | Korpela et al. ............. 209/216 |
| 6,123,902 A | * | 9/2000 | Koch et al. .................... 422/50 |
| 6,143,578 A | * | 11/2000 | Bendele et al. .............. 436/526 |
| 2001/0007770 A1 | * | 7/2001 | Tajima ......................... 436/47 |

FOREIGN PATENT DOCUMENTS

| | | |
|---|---|---|
| EP | 687 505 | 12/1995 |
| WO | WO 87/05536 | 9/1987 |
| WO | WO 95/00247 | 1/1995 |
| WO | WO 96/12959 | 5/1996 |

* cited by examiner

Primary Examiner—Long V. Le
Assistant Examiner—Pensee Do
(74) Attorney, Agent, or Firm—James C. Lydon

(57) ABSTRACT

A device for transfer suitable for capturing and releasing microparticles binding an immobilized substance, which includes a magnet as well as either an extendable membrane, shapable membrane or magnet's coating such that the membrane or coating pressing tightly against the magnet's surface separates the magnet from the microparticles but does not substantially weaken the magnetic field directed at the microparticles. Also disclosed is a method for transferring a microparticle immobilized substance from a first vessel to a second vessel where the microparticles are of a magnetic or magnetizable material or the microparticles are attached to a magnetic or magnetizable body and the microparticles with the substance immobilized thereupon are captured with the aid of a magnet submerged in the first vessel, the magnet along with the microparticles captured thereupon are transferred to the second vessel and released from the magnet's influence.

27 Claims, 9 Drawing Sheets

Figure 1A:
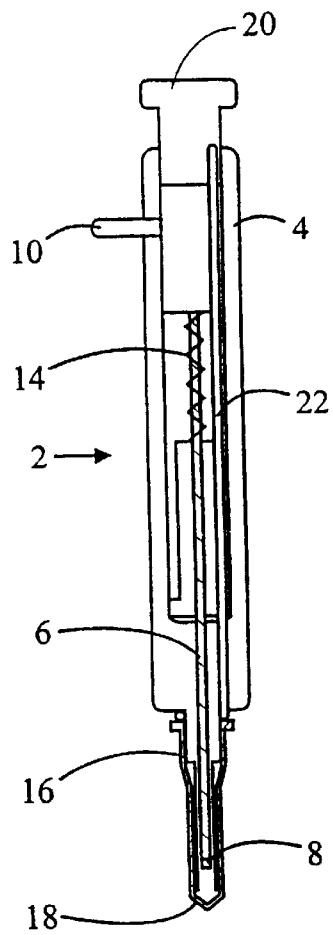

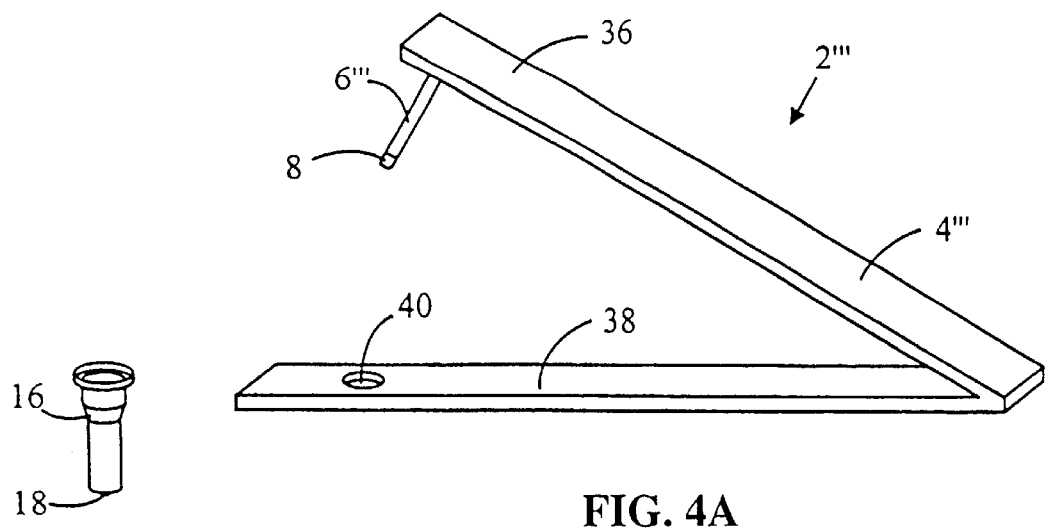
FIG. 4A
FIG. 4B
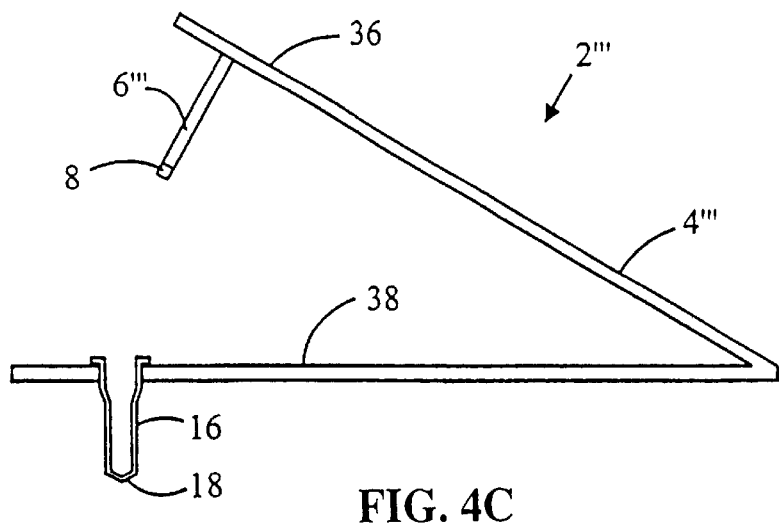
FIG. 4C
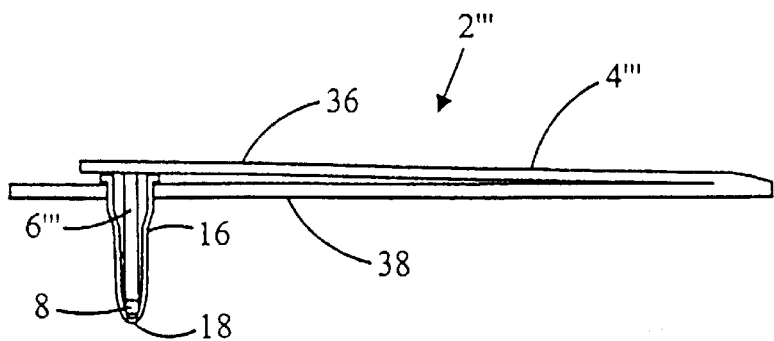
FIG. 4D

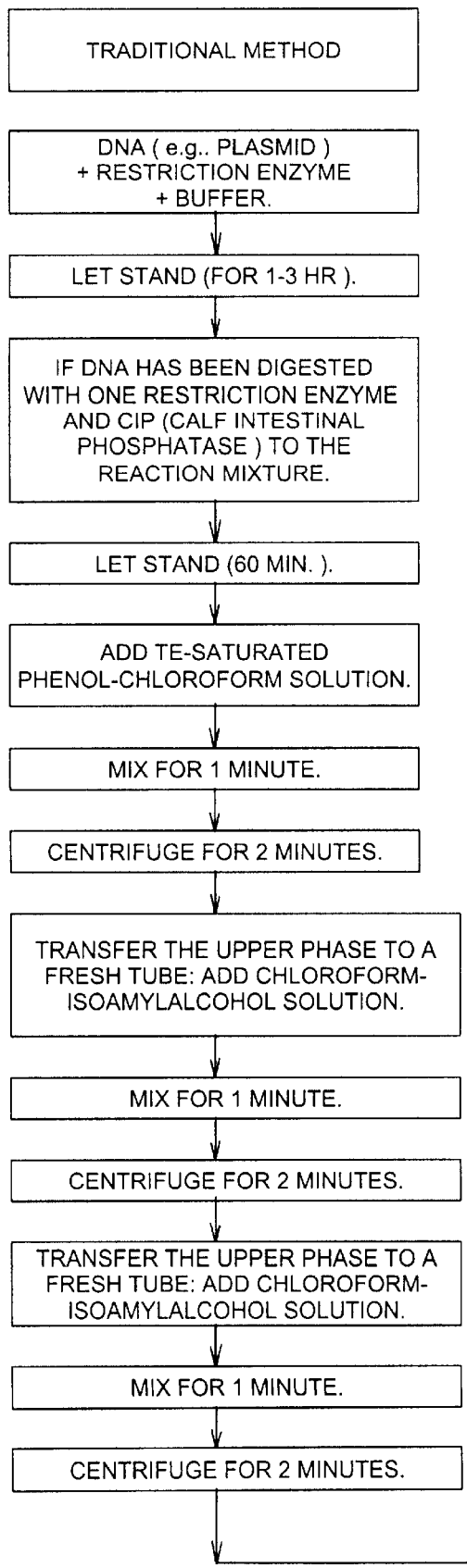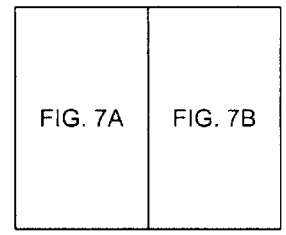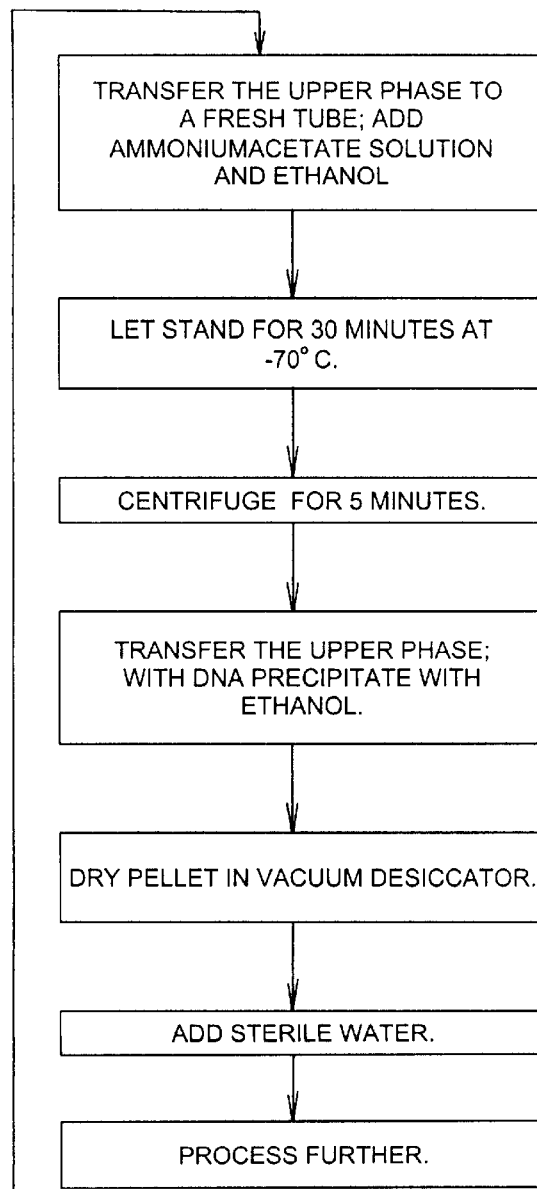
FIG. 7
FIG. 7A

SCHEME 2

MAGNETIC PARTICLE TRANSFER DEVICE AND METHOD

The invention relates to a method for transfer of a substance immobilised to magnetic or magnetisable material with the aid of a magnet. The invention is characterised in that the magnet used for transfer is separated from the material to be transferred by an extendable membrane, shapable membrane or by coating of the magnet.

TECHNICAL BACKGROUND

In the traditional method for separating magnetisable material a magnet which is outside the vessel is used. The magnetisable material is left in the vessel and surrounding solution is removed from the vessel.

By introducing the magnet into the solution great advantages are obtained when collecting magnetisable material compared to the traditional methods. It is especially remarkable that in this case the magnetisable material can simply and efficiently be removed from the vessel. When introducing the magnet into the solution the distance of the magnet from the magnetisable material is shorter than when using an outside magnet. Also, due to the fluid's surface tension collecting magnetisable material left in the solution interface is more efficiently accomplished when the magnet is introduced into the solution.

Patent literature presents numerous devices for separating magnetisable material. The international patent publication WO 87/05536 discloses a separation device within which a permanent magnet moving inside a plastic sleeve can be used to transfer magnetisable material from one vessel to another. The Finnish patent publications (FI 86 05002, FI 95 03669, FI 97 01665, FI 97 01666, FI 97 01667 and FI 97 01668) likewise disclose various methods based on the use of a permanent magnet for transfer of magnetisable material from one vessel to another. The patent publications U.S. Pat. Nos. 4,272,510, 4,649,116 and 4,751,053 disclose magnetic material transfers based on the use of an electromagnet mainly in RIA and EIA assays. The patent publication U.S. Pat. No. 5,567,326 discloses equipment for separation of magnetic particles from the non-magnetic reaction solution with the aid of a steel pin magnetisable with a permanent magnet. Typically, the equipment would include a multiwell reaction plate where magnetic particles can be separated concomitantly in many neighbouring reaction wells using a transfer device with many magnetisable pins. The method described in the patent publication U.S. Pat. No. 5,567,326 is very tedious to use. The unprotected steel pins need to be washed or sterilised in between each time of use. There is a serious risk of contamination in the aforementioned method should the washing not be sufficient.

Magnetic particles have been described in numerous patent publications, for example U.S. Pat. Nos. 3,970,518; 4,018,886; 4,230,685; 4,267,234; 4,452,773; 4,554,088; 4,659,678; 4,978,610; 5,200,084; and 5,705,628. Particle using technology became very popular in for instance immunoassays. Using magnetisable particles for separation of bound antigen-antibody complex from the unbound fraction in immunoassays offered major advantages both in reaction speed and practicality of separation.

Magnetic particles in reaction solution with bound biological material, e.g. cells or an antibody, have been, after the reaction has taken place, secured with the aid of the magnet outside the vessel into a certain location whereupon the solution can be removed without magnetic particles leaving the vessel.

Use of magnetic particles is beneficial because when handling samples, no expensive or space consuming instruments are needed, such as centrifuges, vacuum pumps or chromatographic columns. Magnetic particle applications are simple to perform and volumes used thereupon can vary according to use from small to large.

For the present, magnetic particles are used amongst others in immunoassays, separating cells and bacteria, isolating nucleic acids as well as purification of proteins.

In molecular biology many operations such as isolating and/or transferring nucleic acids as well as using restriction or nucleic acid modifying enzymes pose problems. Among those encountered are inactivation of enzymes, extraction with solvents and star-activity.

Traditionally nucleic acids are isolated and transferred by means of various precipitations and solvent extraction. Some compensatory methods have been presented as aid in nucleic acid management However, these methods are in general expensive and require centrifugation steps. In addition, in some of these methods recovering the nucleic acid in a sufficiently small volume after the operation is difficult.

In methods of molecular biology, where DNA or RNA is manipulated, use is made of restriction enzymes as well as of DNA and/or RNA modifying enzymes. The use of these enzymes is of essential importance in almost all work in the field of molecular biology. The most pre-eminent enzymes in molecular biology labs are the restriction enzymes. These enzymes have made possible major developments in the field. Using restriction enzymes or nucleic acid modifying enzymes in molecular biology applications is mainly routine work which in many cases involves tedious intermittent stages. A good example is provided by the operations needed to eliminate restriction enzyme activity after their use. Many restriction enzymes require phenol extraction in order to inactivate them after use. Phenol extractions are very tedious and from the point of view of the user unpleasant processes. Furthermore, a lot of hazardous waste is generated in these extractions. Commercial manufacturers suggest for many restriction enzymes inactivation by heat treatment whereas in practice users often perform a phenol extraction to insure inactivation of the enzyme. After heat treatment a large percentage of enzyme activity may still remain. Because one has not been able to remove restriction enzymes with currently known techniques the problem has been solved by inactivating enzymes, e.g. by heat or phenol extraction. Another disadvantage is that the used, expensive enzyme can not be reused. Less time consuming but otherwise problematic are various spin columns for purifying DNA from reaction solution. The use of these columns is very expensive, and they are not applicable for removal of many enzymes from DNA solution. Even in this case the retracted enzyme can not be reused.

Phenol extraction is required for inactivation of even many other enzymes commonly used in the field of molecular biology. As examples can be mentioned CIP (Calf Intestinal Phosphatase) and Proteinase K.

No unproblematic means have been presented for transferring and washing restriction enzymes or nucleic acid modifying enzymes. As an example of a problem might be mentioned the star-activity caused by the glycerol used in restriction enzyme storage solution. By this is meant the capacity of restriction enzymes to cut DNA unspecifically, i.e. in places where cutting is not wanted. Commercial restriction enzymes are generally provided as 50% glycerol containing solution. In normal use, a very small amount of restriction enzyme is added to the reaction, even less than 1 μl. If the glycerol content in reaction mixture is too high, it poses, in many cases, a big problem mainly because of the occurrence of star-activity. This sets limits for many molecular biology applications in regard of restriction enzyme use. Another important fact is that it is recommendable to maintain the total volume of the reaction mixture as low as possible in order to have a sufficiently fast enzyme reaction. Commercial restriction enzymes are generally available in one, or at the most two standard concentrations (U/ml). If a great amount of restriction enzyme is wanted in the reaction the glycerol content in reaction solution reaches too high a level. As a result there is star-activity and reaction kinetics are markedly slowed down.

Patent literature suggests preparations in which restriction, or other in molecular biology commonly used, enzymes have been immobilised on a solid support. International patent publication WO 92 15674 suggests immobilising restriction enzymes as well as nucleic acid modifying enzymes onto a surface made of polymer or glass fibre. U.S. Pat. No. 4,342,833 also describes immobilised restriction enzymes using CNBr activated agarose as solid support. On a general level, using magnetic particles in enzyme immobilisation is described in patent publication U.S. Pat. No. 4,698,302 even though in this patent publication there is no mention of enzymes used in the field of molecular biology. In the aforementioned patent publication the separation of magnetic particles was traditionally accomplished with an outside magnet.

In the field of molecular biology capturing of particles poses problems due to the small volumes of fluid in these applications. An acknowledged technique from the fields of cell biology or immunochemistry is not applicable in molecular biology because of the extremely small quantities of liquid used in this field, e.g. 10–100 μl, when corresponding quantities in the field of immunochemistry are several millilitres in magnitude and in the field of cell biology typically 10–100 ml.

Processing cloudy samples or samples containing solid material with magnets traditionally located outside the reaction vessel also poses problems because magnet particles are hard to cleanse of turbidity causing fine particles.

When using traditional outside magnets magnetic particles can not be processed directly transferring them from one reaction vessel to another but have to be processed indirectly by attaching the particles to the reaction vessel wall and changing the surrounding solution with the aid of a pipette.

In the field there is a need for a method that is readily suited for handling small volumes, which is simple to perform, easily automated and readily applicable in various fields.

PURPOSE OF THE INVENTION

The purpose of the invention is to accomplish an equipment and a method to ease the handling of target materials that are bound specifically or unspecifically to a magnetic or magnetisable material. In particular, the invention aims to provide easily miniaturised equipment and methods suitable for handling of small sample volumes.

The equipment and method will be used for many widely varying applications such as immunoassays, cell and virus separations, for isolating and purifying nucleic acids as well as for protein purification. The method is particularly suited for isolating, transferring or purifying nucleic acids.

In addition the equipment and method described herein will be used for handling difficult sample materials, such as cloudy samples or samples containing solid material.

Furthermore, the invention strives to accomplish a device for transfer with which magnetic or magnetisable microparticles, including attached thereupon target material, are easily trapped and eventually released. The device for transfer may be of a type that handles simultaneously only one, or more samples. The method may be totalled as a product that comprises the device for transfer with accompanying separation membrane or coating, reagents needed and with which dosage, washing and recapture of magnetic or magnetisable microparticles is easily accomplished.

In particular, the invention aims to provide a method with which the restriction or other enzyme that is used in the field of molecular biology which is immobilised on microparticles can be dosed and transferred from the enzyme containing vessel to the reaction vessel and eventually be removed and recaptured from the reaction vessel. This invention strives amongst other things to increase the ease of use of enzymes used in molecular biological methods and applications and to the reuse of expensive enzymes. By the current method the immobilised enzyme can be washed free of glycerol or other substance interfering with the reaction before it is delivered to the reaction vessel.

The purpose is also to provide a method for protein purification. By the method according to the invention, purifying proteins is markedly easy and proteins may be concentrated at the same time. In protein purification, use can be made of either unspecific or specific protein binding to the magnetic or magnetisable support material.

With this method the dosage of microparticles to a vessel, collecting and transferring them therefrom is easily automated in applications mentioned.

The present invention makes it possible to combine at will procedural steps made up of handling nucleic acids (isolation, transfer, purification) and using bound enzymes as well as allows combination with traditional methods according to the needs of the application at hand.

DESCRIPTION OF THE INVENTION AND PREFERRED EMBODIMENTS

The characteristics of the invention will emerge from the appended claims. Thus the object of the invention is an equipment and a method for transfer of a microparticle inmmobilised substance from a first vessel to a second vessel. The microparticles are of magnetic or magnetisable material or the microparticles have been attached to a magnetic or magnetisable body. Microparticles with the immobilised substance are collected by aid of a magnet submerged in the first vessel, the magnet along with captured microparticles is transferred to the second vessel and the microparticles are released from the magnet's influence. It is characteristic of the invention, that the magnet's surface is separated from the microparticles either with the aid of an extendable membrane or shapable membrane or magnet coating so that the membrane or coating does not essentially weaken the magnetic field directed at the microparticles.

The method according to the invention is especially applicable to fields where small volumes are handled.

In the present application the concept "substance" means any substance immobilised to microparticles that may occur in the application fields of the invention.

"Substance" can therefore stand for e.g. a protein, polypeptide or hapten. The protein can be for example an enzyme, antibody or receptor. The polypeptide can be for example a polypeptide hormone. By hapten are meant low molecular compounds such as lectins, hormones, drugs, pesticides or toxins. Thus also the bioaffinity components used in immunoassays (an antibody or antigen or a complex thereof), for example, and the bioaffinity components used in protein purification (such as a biotinylated protein or streptavidin or a complex thereof) will be included in the concept of "substance".

"A substance" can thus be also a restriction enzyme, modifying enzyme or some other enzyme used in molecular biology, e.g. a protease like proteinase K. As examples of DNA and/or RNA modifying enzymes the following can be mentioned: CIP (Calf Intestinal Phosphatase), *Escherichia coli* alkaline phosphatase, exonucleases (e.g. P1 nuclease, S1 nuclease), ribonucleases, RNases (e.g. pancreatic RNase RNase H, RNase T1, RNase M, RNase T2), DNA ligases, RNA ligases, DNA polymerases, the Klenow enzyme, RNA polymerases, DNA kinases, RNA kinases, terminal transferases, AMV reverse transcriptase and the phosphodiesterases. The application of these and other DNA and/or RNA modifying enzymes is extremely varied in both research and applications of molecular biology. "A substance" can be a nucleic acid, any one or two stranded nucleic acid and especially DNA, RNA, mRNA or cDNA. A nucleic acid can also be PNA (polyamide nucleic acid).

"A Substance" can also be a cell such as a T cell, leukocyte, parasite (e.g. *Giardia lamblia*) and bacterium (e.g. Salmonella sp., *E. coli* 0157:H7, *Listeria monocytogenes, Staphylococcus aureus, Mycobacterium tuberculosis*).

"A substance" can even be a virus, such as HIV, rotavirus, canine rotavirus, arabis mosaic virus or soybean mosaic virus.

The concept "microparticle" means in this context rather small particles, preferably in the range of 1.0–10 µm. The microparticle on which a substance is immobilised can be made of a magnetic or magnetisable material. According to another alternative the microparticle itself on which the substance is immobilised can be non-magnetic. In this case the microparticle is suitably attached to another body that is of a magnetic or magnetisable material.

The concept "immobilised", when discussing substances immobilised on microparticles, means in this context all such ways, in which the surrounding solution gets in contact with the substance attached to the particle, of attaching or binding the substance, which is to be transferred, to microparticles for the duration of the method of the invention or at least the transfer stages thereof. The immobilised substance can for example be attached on the surface of the particles or it can be captured in a cage like body. "Immobilised" can thus mean also reversible immobilisation in those cases where the substance to be transferred is attached to microparticles for some stages, e.g. transfer stages, and released therefrom at the end of these stages.

"Attaching" a substance to microparticles can be accomplished by means of covalent bonding, e.g. making use of the amino or carboxyl groups present on the support. Alternatively, "attachment" can be accomplished using a bioaffinity couple, e.g. biotin/streptavidin couple. One way to proceed is to produce the substance to be immobilised, e.g. an enzyme, by recombinant DNA techniques, e.g. in *Escherichia coli* bacterial cells, making a special affinity tail on the enzyme. This affinity tail will bind to the microparticles that have suitably attached thereupon some component that will avidly bind the affinity tail in question. The affinity tail may be a low molecular compound, polypeptide or protein. With this arrangement efficient use could be made of microparticles in purifying the desired enzyme and at the same time, the microparticle bound enzyme would be immobilised on the microparticle surface, ready to be used in the method described in the invention.

"Attaching" a substance to the microparticles can also be an unspecific non-covalent event such as adsorption. As an example direct attachment of DNA to a glass surface can be mentioned.

The concept of "magnet", by which the particles are captured, means in this context a material that is either permanently magnetic or that is magnetizable, or a combination of the aforementioned. Ferromagnetic material can suitably be combined with a permanent magnet and/or with an electromagnet. Magnetisation can be carried out either by an electric field or a permanent magnet that is brought into contact with the material to be magnetised. According to the invention, the shape, and size of the magnet may vary.

The concept "magnetic or magnetisable material" includes paramagnetic, superparamagnetic or ferromagnetic materials. Especially suitable as particle material is any of the superparamagnetic materials. The superparamagnetic particles form for themselves by influence of an outside magnetic field a magnetic field that disappears when the outside magnetic field is removed. Therefore the particles stay separate and do not precipitate which is beneficial to their use. Many commercial manufacturers supply magnetic particles (both paramagnetic and superparamagnetic particles), such as Bangs Laboratories Inc., Dynal A. S., Advanced Magnetics Inc., Scipac Limited, Paesel+Lorei and CPG Inc. Choice can be made amongst differently sized magnetic particles that are activated beforehand and in various ways. Also, magnetic particles that are modified in many different ways are available. As examples can be mentioned magnetic particles that are either carboxy or amino modified. Generally magnetite is bound to a polymeric support such as latex or cellulose. CPG Inc. makes magnetic particles made of porous glass. In all the aforementioned magnetic particles small magnetite crystals (1–20 nm) have been dispersed in polymer and/or glass which is polymerised producing a magnetisable particle. Among others, Prolabo produces magnetic particles that have magnetite in a controllable way only in the core of the particles. This is important, because iron must not be released into the reaction solution in many molecular biological applications such as in a PCR reaction. Iron released in the solution inhibits progress of the reaction in PCR reactions. A magnetic or magnetisable material may also be included in a gel-like substance.

In the method according to the invention the surface of the magnet used is separated from the microparticles by a separate "membrane" or "coating". "The membrane" can be an extendable membrane and/or a shapable membrane. When the magnet is immersed in the vessel in order to capture the microparticles the latter will accumulate to the surface of the membrane or the coating. The magnet along with the microparticles accumulated on the membrane or coating are thereafter taken into a second vessel. In the second vessel the permanent magnet is drawn away from the membrane—this will release the microparticles due to the weakened magnetic field. In case of an electromagnet a magnetic field is created for the collecting event and for releasing the magnetic particles the magnetic field is removed. In case of a magnetisable magnet the magnet is magnetised by connecting a permanent magnet to the magnetisable magnet in order to collect and transfer the magnetic particles and the permanent magnet is detached from the magnetisable magnet in order to release the magnetic particles.

The "membrane" described in the invention means e.g. a membrane sheet, roll or preshaped membrane. The membrane can suitably have connected thereto reinforcement or support elements for ease of handling. The membrane material can be flexible and/or extendable as long as it can be shaped to suit the magnet used according to the invention. The membrane is preferably thin or it can be made thin by extension. The membrane material is preferably an elastomeric material such as silicone rubber, polyurethane, fluoroelastomer, polychloroprene or chlorosulfonated polyethylen.

The "coating" described in the invention means a separate surface that is fixed on the magnet. A coating can also be renewed or changed.

An object of the invention is also a device for transfer that is suited for capturing microparticles and releasing the same. The device for transfer is characterised in that the magnet's surface is separated from the microparticles either by an extendable membrane, shapable membrane or coating so that a membrane or coating, which tightly adheres to the magnet's surface, separates the magnet from the microparticles but does not essentially weaken the magnetic field targeted at the microparticles.

It is essential that when introducing the device for transfer into the fluid in order to collect the magnetic particles in solution a magnetic field be applied thereon so that the magnetic particles accumulate, due to the magnetic field applied, to the device for transfer. The device for transfer according to the invention can be realised so that the microparticles accumulate suitably on the outer surface of the membrane. The magnet may be designed so that the microparticles will accumulate either on a small area (for example, on the device tip) or on a substantially larger area.

The magnetic particles do not accumulate directly onto the metallic surface of the magnet but around the protective membrane or coating surrounding the magnet. It is most preferred that the protective membrane or coating be an extremely thin protective layer that sits tightly on the magnet or around the same whereby creating in the solution the biggest possible magnetic field force. The protective layer can be a special inert (fixed, permanent) layer of coating forming agent around the magnet, e.g. teflon, silane etc. This is a case that comes in question in particular when using an electromagnet or a magnetisable magnet. The protective membrane can be shapable and/or extendable. In the event of collecting microparticles, the protective membrane may even be extended, thereby decreasing membrane thickness and enforcing the magnetic field. With the device for transfer according to the invention microparticles can be transferred from small volumes of fluid using an extremely small magnet in small vessels.

The device for transfer and the sample processing system both according to the invention is presented in greater detail in the following drawings where:

FIG. 1A presents an axial cross-sectional view of a device for transfer according to the invention equipped with an extendable membrane based on the use of a permanent magnet where the magnet is in the particle releasing position.

Figure 1B:
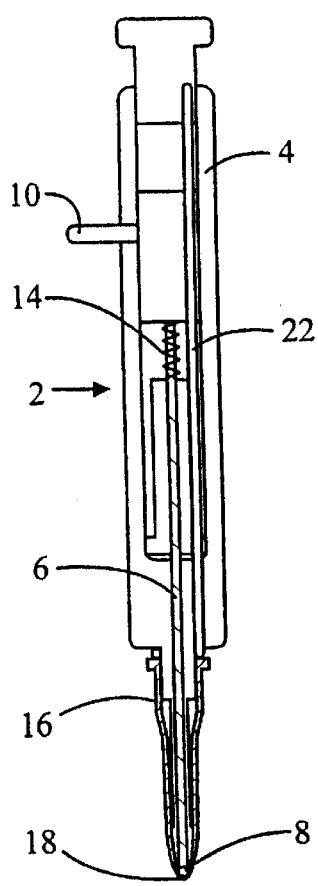

FIG. 1B presents a device for transfer according to FIG. 1A as an axial cross-sectional view where the magnet is positioned for collection and transfer of particles.

Figure 1C:
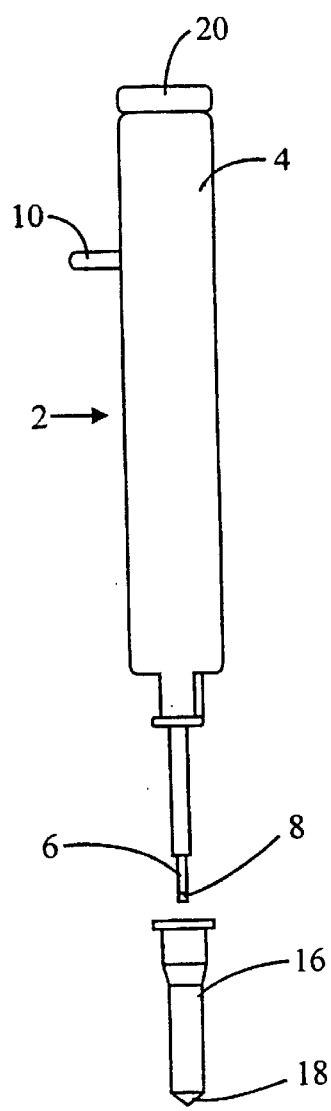

FIG. 1C presents a device for transfer according to FIG. 1A and FIG. 1B, from which the nose comprising a membranous base is detached.

Figure 1D:
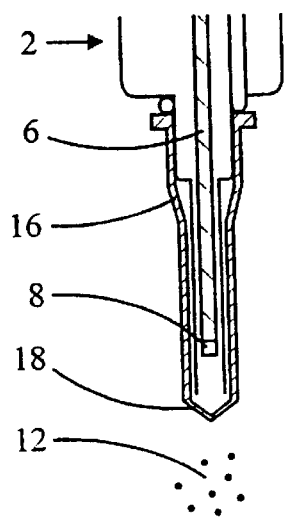

FIG. 1D presents the lower part of the device for transfer as a partial enlargement of FIG. 1A.

Figure 1E:
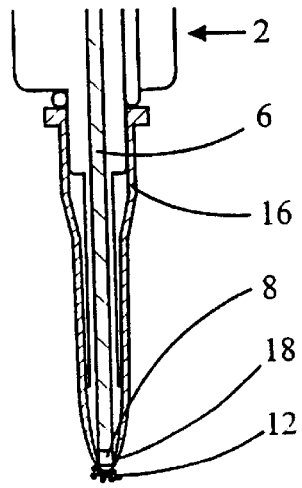

FIG. 1E presents the lower part of the device for transfer as partial enlargement of FIG. 1A.

Figure 2A:
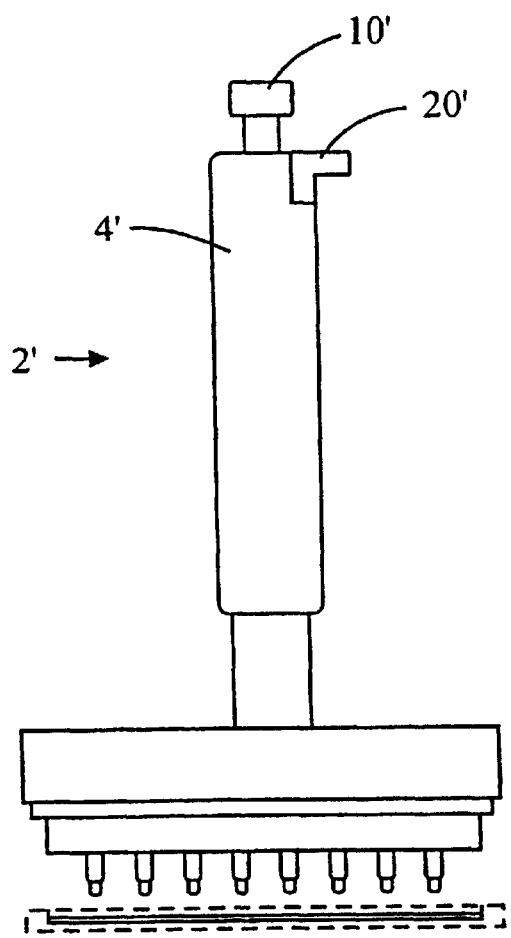

FIG. 2A presents a device for transfer for handling multiple samples simultaneously.

Figure 2B:
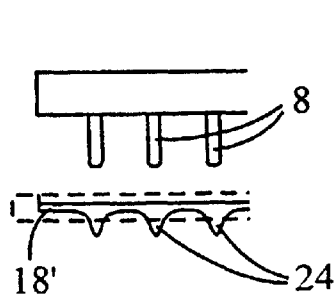

FIG. 2B presents the lower part of the device for transfer as a partial enlargement of FIG. 2A, where the magnets of the device for transfer have a common preshaped membrane.

Figure 2C:
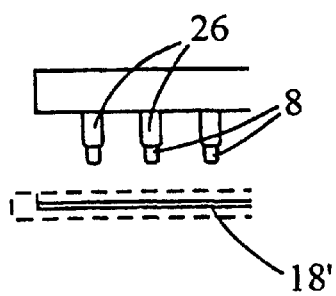

FIG. 2C presents the lower part of the device for transfer as a partial enlargement of FIG. 2A, where the magnets of the device for transfer have sleeves and a common membrane.

Figure 2D:
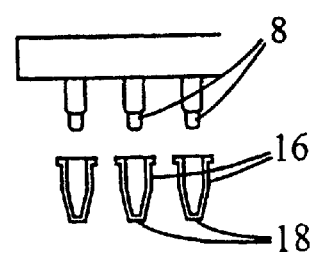

FIG. 2D presents the lower part of the device for transfer as a partial enlargement of FIG. 2A, where the magnets of the device for transfer have separate noses with a membranous base.

Figure 3A:
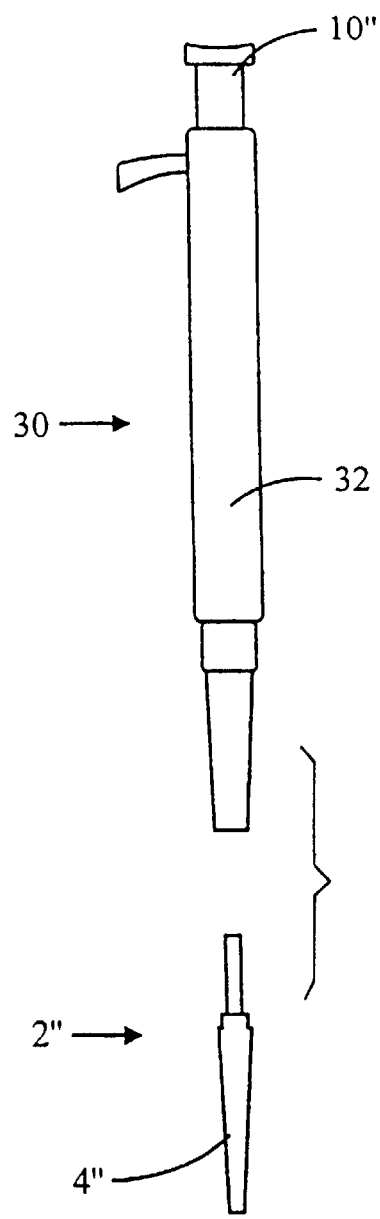

FIG. 3A presents a pipette's body and a device for transfer that is attached to the pipette's body during operation.

Figure 3B:
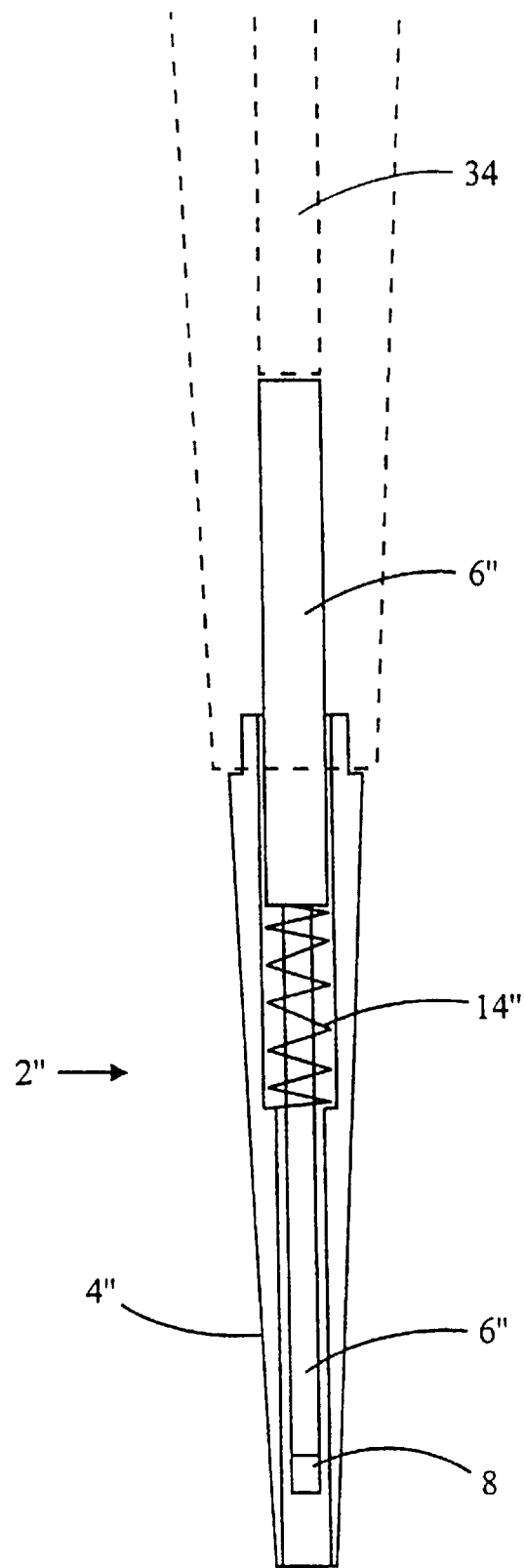

FIG. 3B presents the device for transfer according to FIG. 3A as an enlarged axial cross-sectional view.

FIG. 4A presents an embodiment of the invention which represents a tweezers-like, simplified device for transfer.

FIG. 4B presents an enlargement of a nose with a membranous base which suits the embodiment according to FIG. 4A.

FIG. 4C presents a cross-sectional view of the device for transfer according to FIG. 4A, where the magnet is in the microparticle releasing position.

FIG. 4D presents a cross-sectional view of the device for transfer according to FIG. 4A, where the magnet is in the rmicroparticle collecting position.

FIGS. 5A–5E present a device for transfer based on the use of a magnetisable magnet.

Figure 6:
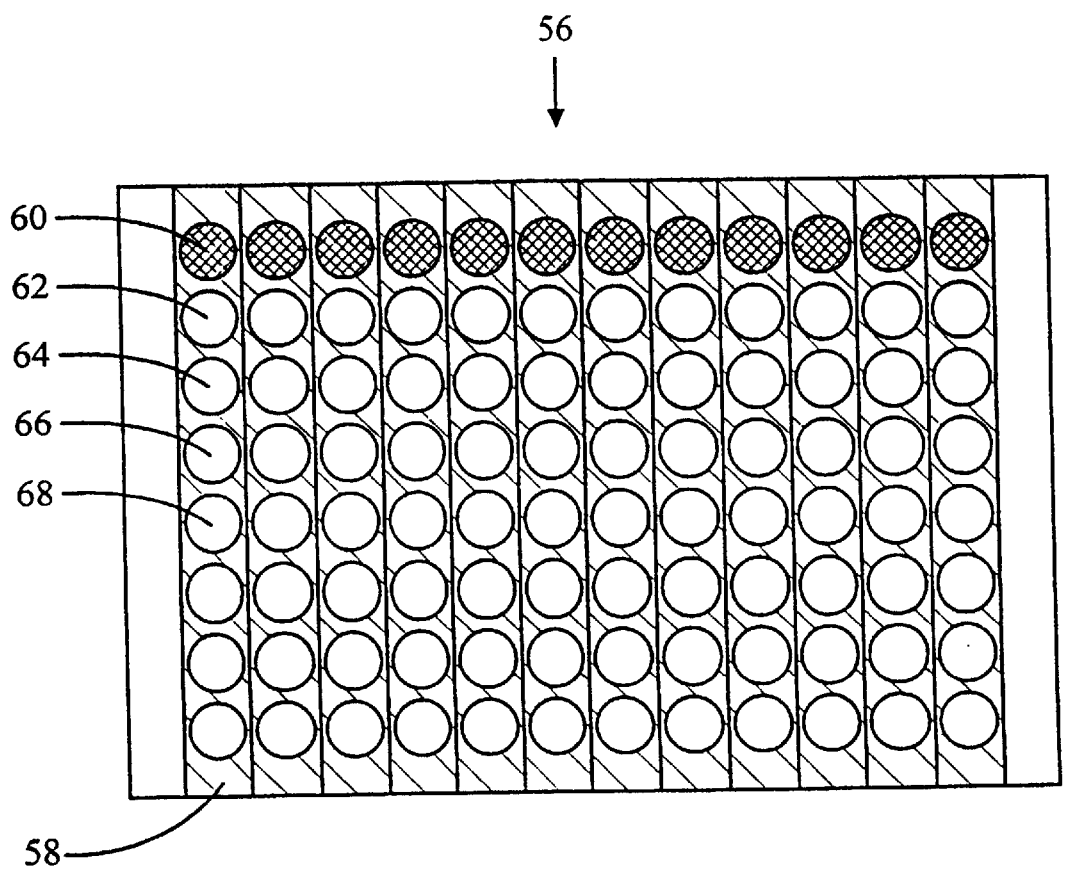

FIG. 6 presents a sample processing system according to the invention.

Figure 7B:
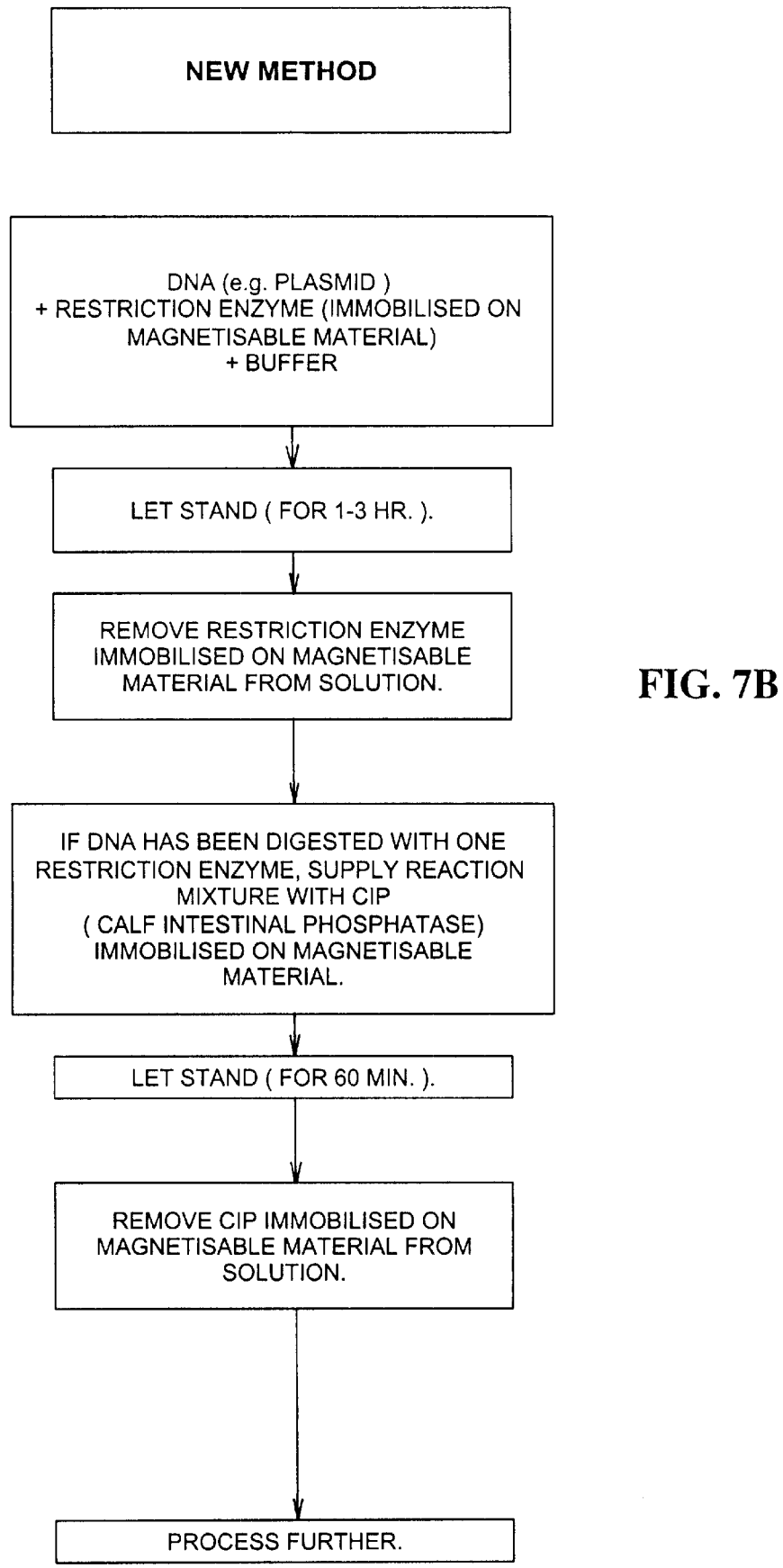

FIGS. 7, 7A and 7B compare an embodiment of the present invention to a traditional method which employs enzyme inactivation.

Figure 8:
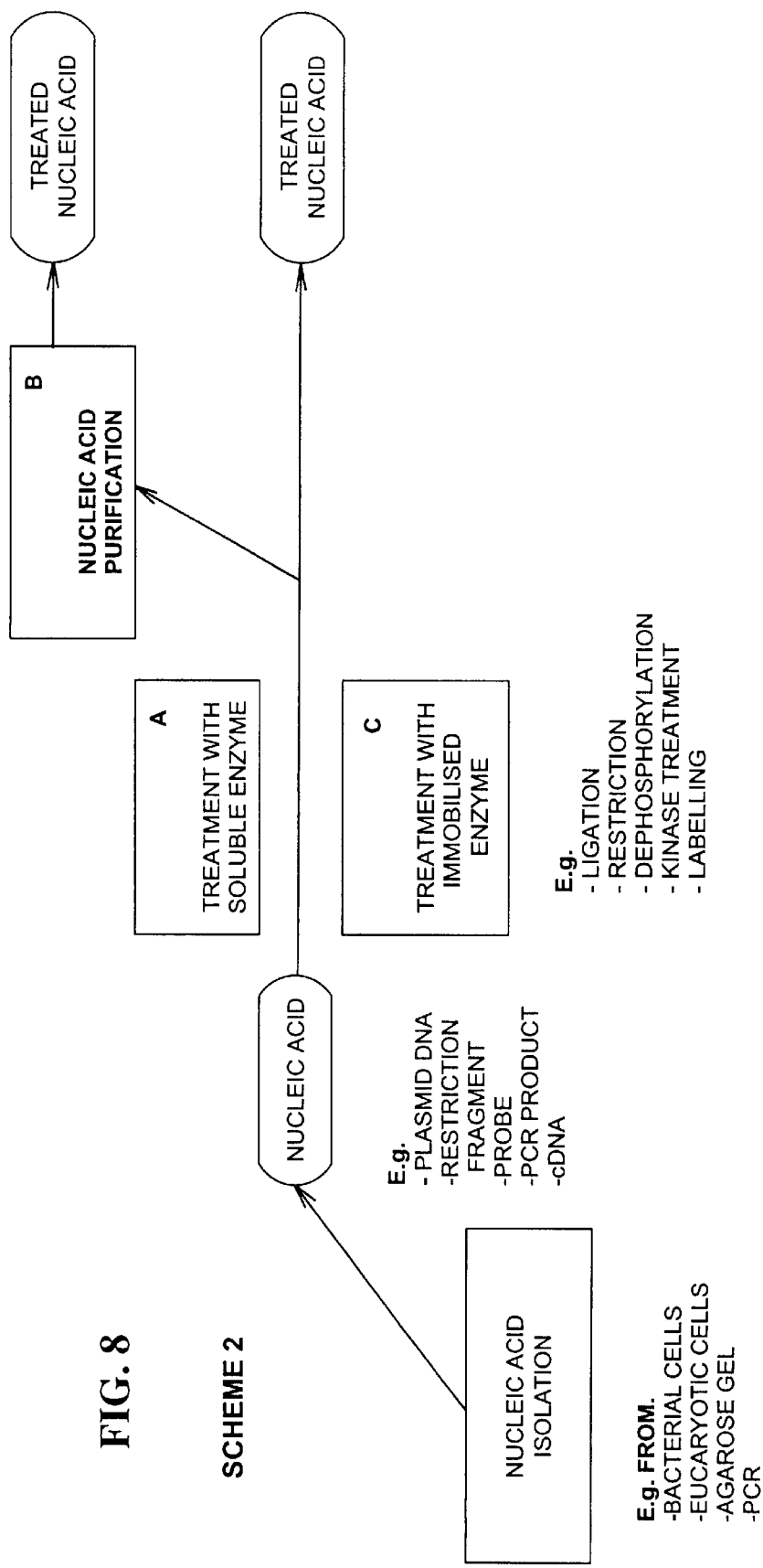

FIG. 8 depicts an embodiment of the invention application to nucleic acid isolation, enzyme processing and purification.

FIGS. 1A–1E present a device for transfer 2 that is suitable for capturing and releasing microparticles. A bar 6, which can be axially moved back and forth and serves as an attachment arm for a magnet 8, is placed in a tube-like body part 4. The bar 6, with at its one end the magnet 8, can be pressed with the aid of lever 10 downwards to the particle 12 collecting position from which the spring force of spring 14 returns it to the particle 12 releasing position when lever 10 is not pressed. In this solution, the magnet 8 may be a powerful NdFeB (neodyme, iron, boron) permanent magnet and the bar 6 may be of magnetism conducting material. One end of the body part 4 may be fitted with a nose 16 with a membranous base 18. In this solution, the nose 16 can have as material extendable silicone rubber at the thickness of 0.1–1.0 mm. The magnet's 8 surface can be pressed against the membranous base 18 of the nose 16 to attach the microparticles 12 to the base 18 (FIGS. 1B and 1E). The microparticles 12 will detach when moving the magnet 8 away from the membrane 18 (FIGS. 1A and 1D).

The lever 10, which is operated by pressing with a finger, is connected to the bar 6 moving inside the body part 4 (FIGS. 1A and 1B). It may be locked into collecting and transfer position. The lever 10 is influenced by an upwards acting return spring 14. When the lever 10 is pressed to the utmost downward position the bar 6 and at its end the magnet 8 will be pressed to the nose 16 so that the membranous base 18 of nose 16 will extend and press tightly against the magnet (FIGS. 1B and 1E) so as to bring the microparticles 12 under the influence of a magnetic flux that is as strong as possible. The body part is also fitted with a lever 20 (FIGS. 1A–1C) with connected thereon a bar 22 with the aid of which the nose 16 pressed against the lower part of the device for transfer 2 may be detached from the body 4 of the device for transfer 2 (FIG. 1C). Once the microparticles 12 have been transferred to the desired vessel the nose 16 can be detached.

The above described device for transfer can be realised according to the constructional principles presented above allowing for modifications as to the locations of various parts, geometry and materials e.g. as called for by ergonomical considerations in various working positions and circumstances.

In FIGS. 2A–2D an embodiment of a device for transfer 2' is presented that can handle multiple samples simultaneously. Functionally the device for transfer may be realised in an equal manner to the device for transfer 2 according to FIGS. 1A–1E as long as care is taken that movements of control organs, such as lever 10' and lever 20', are simultaneously conveyed to each magnet 8 and/or to adhering structural elements.

FIG. 2B presents an embodiment where the magnets 8 have a common membrane 18' preshaped so that each magnet 8 has its own preshaped well or groove 24 on membrane 18'. Then these grooves 24 may be left hanging in the vessel to which the microparticles are being transferred and/or in which the membrane 18' and/or any microparticles that might be adhered thereon are being washed even when the magnets 8 are in the microparticle releasing position. Area 24 preshaped for magnet 8 can be specially designed for each application and accordingly have a shape other than that of the groove 24.

FIG. 2C presents an embodiment where magnets 8 are shoved from sleeves 26 to a microparticle collection and transfer position and then retracted to sleeves 26 for a microparticle releasing position. Thus the membrane 18' can be extended downwards with the aid of the sleeves 26 when wishing to flush any microparticles and/or other substances that might be adhering to the membrane 18' therefrom to the fluids in the vessels with the magnets 8 in the microparticle releasing position.

FIG. 2D presents an embodiment where each magnet 8 of the device for transfer 2' has its own nose 16 equipped with a membranous base 18 quite as in the one magnet 8 equipped device for transfer 2 according to FIGS. 1A–1E. The noses 16 may according to wish be connected to each other in a fixed manner or by means of a separate plate equipped e.g. with suitably sized holes.

The embodiments according to FIGS. 2A–2D may be adjusted as to the number of samples handled simultaneously as well as the magnets' reciprocal positioning and size so that they are suited for the equipment according to standards applying to the application at hand, e.g. suited for 96 or 384 well plates.

The embodiments according to FIGS. 1A–2D are manually operable but they may be modified in order for them to form part of an automated equipment or system.

The embodiment of a device for transfer 2" according to FIGS. 3A and 3B is, to be operable, attached to a pipette's 30 body 32. The body 4" of the device for transfer 2" is attached to the pipette's 30 body 32 suitably, by e.g. threaded mounting, so that it will not detach when operated. The interconnected pipette's 30 body 32 and device for transfer 2" is operated as a device for transfer so that the magnet 8 of the device for transfer 2" is pressed downwards to the magnetic particle collecting position against the bottom part of the nose (which while not presented in FIGS. 3A and 3B is according to the nose 16 portrayed in FIGS. 1A–1E) by pressing the button 10" on the pipette 30. This will cause the pipette's 30 piston 34 to press the bar 6" of the device for transfer 2" against the spring 14" so that the magnet 8 at the lower end of the bar 6" will push against the membranous base of the nose. The spring 14" will return the bar 6" with the magnet 8 attached thereon to the magnetic particle releasing position when the lever 10" is not pressed. The embodiment portrayed in FIGS. 3A and 3B may be realised to fit many kinds of pipette bodies by modifying structural elements.

A simplified embodiment of the device for transfer 2''' is presented in FIGS. 4A–4D. The body 4''' of the device for transfer is tweezers-like in that it consists of two elongated arms 36, 38 joined at first ends and made of a material which makes them flexible so that a spring force strives to keep the second ends of arms 36, 38 apart. A bar 6''' is attached on the second end of the upmost arm 36 which bar in turn has attached to its end a magnet 8. On the second end of the lower arm 38 is a hole 40 where the nose 16 is placed. A nose 16 with a membranous base 18 is portrayed in FIG. 4B. In this embodiment the nose 16 is according to FIGS. 1A–1E. In FIG. 4C the device for transfer 2''' is in the magnetic particle releasing position; when the "tweezers" arms 36 and 38 are pressed together (FIG. 4D) the bar 6''', with magnet 8 attached to one end, will project into the nose 16 and press against its membranous base 18 extending the same so that the membranous base 18 is thinned out and presses tightly against the magnet's 8 surface.

The embodiment described in FIGS. 4A–4D may also be realised in such a way that the arms of the tweezers-like body that connect at their first ends according to the previous embodiment cross each other between the first and second ends in order for the bar and the magnet at its one end to be pressed by the spring force against the membrane on the nose whereupon the device for transfer is in its relaxation mode in the microparticle collection and transfer position. Thus when pressing the arms from their first ends their second ends will separate and the bar, with the magnet attached on one end, will move upwards from the nose and be shifted to the microparticle releasing position.

The embodiment described in FIGS. 4A–4D can furthermore be realised even in other ways, for example so that the first and second arms form parts of one bent body, or that the structure is scissors-like. The spring force can be caused by the material of the arms or by a separate spring. A spring force which strives to bring the arms closer together or further apart is not necessarily applied to the arms in all embodiments but the bringing closer together or further apart might be controlled by the operator based on other structural characteristics such as the scissors-like structure of the device for transfer.

FIGS. 5A–5E present a device for transfer 42 based on the use of a magnetisable magnet. The nose of the magnetisable magnet 46 is noted by the number 44. The magnetisable magnet 46 can be magnetised with an electric field or with the aid of a permanent magnet. The permanent magnet may as in FIG. 5A be presented by the part 52 on the upper part of a device for transfer 42 which magnetises the magnet 46 including its nose 44 when the permanent magnet 52 is brought in contact with a magnetisable magnet 46.

Figure 5A:
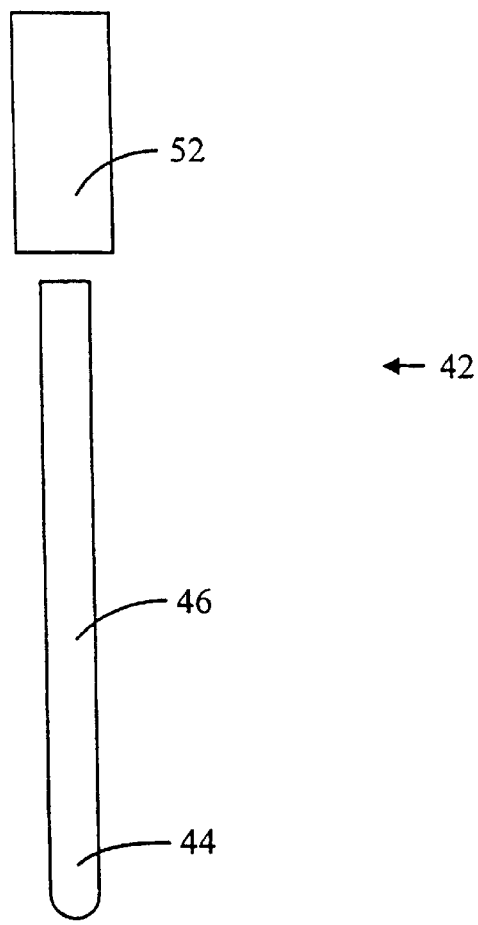
Figures 5B, 5C:
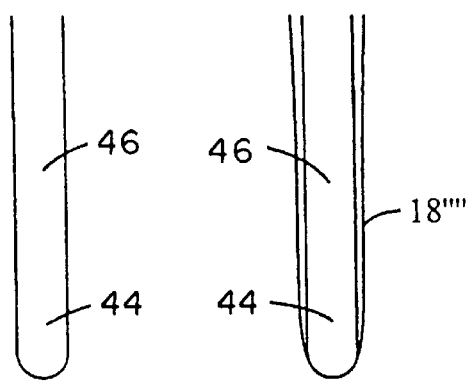
Figures 5D, 5E:
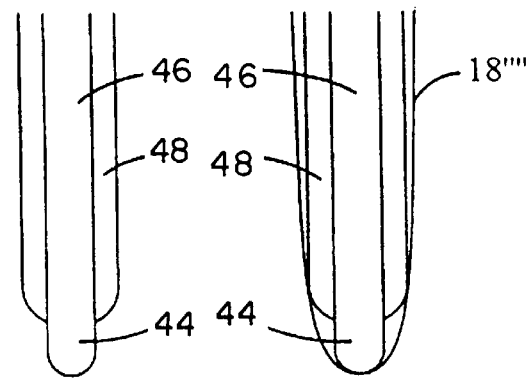

In FIGS. 5A–5C we can see a solution where the magnetisable magnet 46 and its nose 44 are free of any special cover while in FIGS. 5D and 5E we can see a solution where the magnet 46 and partially its nose 44 have been protected with a permanent cover 48. The permanent cover 48 described in FIGS. 5D and 5E can be made of various materials, for example non-ferromagnetic materials such as plastic, and the shape of the cover 48 can be varied.

In FIGS. 5A, 5B and 5D the magnets 46 of devices for transfer and/or the magnet noses 44 have been coated with a suitable coating. The coating can be chosen as hydrophobic or hydrophilic to suit the application. The magnet 46 and/or nose 44 can also be recoated one or several times if needed. The magnet's 46 nose 44 and cover 48 may be coated differently. If the nose 44 has to be washed before reusing the device for transfer 42, this is easily accomplished e.g. with the aid of automated equipment.

The magnet's 46 nose 44 may be equipped with a separate, shapable protective membrane 18''' (FIGS. 5C and 5E). FIG. 5B presents the nose of the device for transfer 42 according to FIG. 5A and FIG. 5C presents this same nose surrounded by the protective membrane 18'''. Due to the thinness of protective membrane 18''' the magnet's field force is good.

By changing the relative positions of magnet 46, its nose 44, cover 48 and/or protective membrane 18'''' to one another one can considerably influence particle collecting characteristics. By suitable design of magnet 46 and/or its nose 44 the device for transfer can be used with small volumes.

A system for DNA purification serves as an example of a system for processing samples based on microparticles. FIG. 6 presents a multiwell plate included in the purification system. Plate 56 has wells 60, 62, 64, 66 and 68 in which various stages of the purification method can be carried out. In the purification method according to this example, the microparticles needed in the method are in well 60 from which they are transferred with the aid of the device for transfer to the wash liquid in well 62 and after the washing to the well 64 into which is added the DNA to be purified which attaches itself to the microparticles. Next, the particles along with the DNA attached thereupon are washed two times in wells 64 and 66. The transfers from one well to another are realised using the device for transfer according to the invention. After the washings the particles along with the DNA still attached thereupon are transferred to well 68 containing the eluent. Once the purified DNA has detached itself from the microparticles the latter are transferred with the aid of the device for transfer away from the well 68, leaving behind the purified DNA. In the purification method according to this example, microparticles can be transferred to the wash liquid in well 62 even directly from a separate storage vessel. In differing methods for processing of samples various proceedings according to each method may be realised in the wells of plate 56, such as stages for heating, cooling, mixing, measuring (analytical methods) and dosage of reagents.

The plate 56 can consist of a series of wells, e.g. strips 58 so that each strip has the wells needed to process one sample aligned. The wells 60, 62, 64, 66 and 68 on each strip 58 form a series of wells that may well comprehend the wells needed to process each and every stage of a multistage processing method. The plate 56 may comprise several aligned strips 58 that may be suitably interconnected.

Dosing may easily be automated with this system. The device for transfer of particles is e.g. first introduced to a first well 60 from which the total amount of microparticles dosed thereto is collected. Then, the device for transfer along with the microparticles attached thereupon is introduced to a second well 62 as need may be or directly to a third well 64. The wells 60, 62, 64, 66 and 68 can even be located on separate plates.

The device for transfer and plate 56 described above can form main components of an automated device. The device may even comprise several devices for transfer that may be connected to a robot controlling their function according to circumstances dictated by the process.

APPLICATIONS OF THE INVENTION

The method according to the invention is applicable for transferring magnetic or magnetisable material in all applications where there is need to bring the substance to be isolated or determined from one vessel to another. These cases are represented amongst others by all methods in which the substance to be isolated (cell, bacteria, protein, hapten) is in a sample matrix that contains lots of particulate matter. Also cases where determinations cannot not be made due to cloudiness or colouring of the sample matrix are preferred embodiments of the method according to the invention. Food or soil samples may be mentioned as examples of problematic sample matrixes.

The method according to the invention applies well even to cases where the substance needs to be concentrated or transferred from one vessel to another. In protein purifications there is a great need for a method by which in addition to purification, the protein's concentration could be increased in a simple and efficient way. In applications of molecular biology that usually contain many stages there is a great need for a simple method for transferring matter (e.g. DNA fragments) from one vessel to another.

The method is also applicable to immunoassays.

Using the invention it is possible to carry out magnetic or magnetisable material transfers described above in differently sized vessels (e.g. an Eppendorf tube, 96 well plate, 384 well plate). The method according to the invention makes it possible to handle samples in very small reaction vessels. Processing extremely small fluid volumes in small vessels is very essential e.g. in the field of molecular biology.

The device for transfer according to the invention can be a hand or stand held device for processing one or several samples simultaneously, it can be a part of a larger apparatus or included in comprehensive, automated equipment.

An embodiment of the invention applicable to nucleic acid isolation, enzyme processing and purification is presented in scheme 2. Using the invention, the nucleic acid can be treated with soluble enzymes (A) whereafter the nucleic acid, without the enzymes, is transferred to another reaction vessel by binding it reversibly to magnetic or magnetisable material (B). The nucleic acid can also be treated with enzymes bound to a magnetic or magnetisable material (C). These enzymes can be used either to process the nucleic acids or to inactivate any enzymes eventually present in the reaction mixture. After processing, the nucleic acid does not require purification because the processing enzymes have already been removed from the reaction vessel with the aid of the device for transfer according to the invention. The invention also allows the use of arbitrary combinations of using soluble and bound enzyme as well as nucleic acid purification in nucleic acid processing.

The method according to the invention is applicable to digesting nucleic acids with restriction enzymes and also to the use of other enzymes used in methods and applications of molecular biology. The enzyme immobilised to microparticles is introduced to the reaction vessel where the enzymatic reaction is allowed to proceed for the time needed. After the reaction, the microparticles along with the enzyme bound thereupon are removed from the reaction vessel. Thus inactivation of the immobilised enzyme becomes unnecessary. The immobilised enzyme used in the reaction is transferred to a washing well where any remnants of the reaction mixture are washed away. The immobilised enzymes once washed are transferred to a vessel supplied therefor in order to be reused.

After processing with restriction enzymes the reaction vessel can be supplied e.g. with microparticle immobilised CIP enzyme (Calf Intestinal Phosphatase) or some other immobilised enzyme necessary in the application at hand. When using them, the method described above is applied and the same benefits are obtained as when using restriction enzymes.

Because the enzymes once used can be removed a stage for enzyme inactivation is eliminated in total. At the same time, the method is substantially simpler and faster than the traditional one with enzyme inactivation. In the comparison presented in scheme 1 for a case of a simple restriction enzyme and CIP treatment it can be seen that many stages in the new method are omitted as unnecessary.

The invention provides also for a method where a microparticle immobilised protease (e.g. proteinase K) can be used in order to inactivate a soluble enzyme present in the reaction vessel. Proteinase K is a very common enzyme with multiple applications. Unfortunately, this enzyme is very stable, and requires an efficient inactivation (e.g. phenol extraction). According to the invention described, proteinase K can be used in immobilised form and then removed very efficiently from the reaction vessel. In this mode, the immobilised proteinase K complements the benefits of the invention as a general inactivation procedure of enzymes. This mode is very beneficial especially e.g. in cases where the enzyme to be inactivated cannot not be brought to an immobilised form, the enzyme to be inactivated is present in the reaction mixture as a contaminant or when wishing to ascertain total enzyme inactivation in the reaction mixture. The immobilised proteinase K complements large scale use of the invention in, amongst other, applications of molecular biology.

The method according to the invention is applicable to nucleic acid isolation and purification. As applications can be mentioned for example purifying plasmid DNA, cDNA, mRNA and purification of PCR amplification products. The invention allows purification of nucleic acids also from difficult sample matrices.

The method according to the invention has especially beneficial applications also in fields where enzymes immobilised to magnetic material bring additional benefits compared to present methods.

With the method according to the invention, the inmmobilised enzyme can be collected from reaction mixture for reuse. With the method, the immobilised enzyme may also be transferred from a dosage vessel to the reaction mixture. When required, microparticles captured with the aid of a magnet can be introduced to a washing liquid in order to wash away glycerol or other preservative before introducing the same to the reaction mixture. In the washing vessel the mnicroparticles may, as need may be, be released of the magnetic field in order to release the particles and make the wash more efficient.

The invention is well suited also for protein purification. Especially commendable ways for protein purification are the diverse affinity purification methods. With the method described in the invention, proteins can be purified also from a very difficult sample matrix (e.g. containing disrupted cells), and the proteins may be eluted into a very small volume.

The device for transfer according to the invention allows for handling numerous samples when connected to automated equipment. The invention described allows for handling samples in very small fluid volumes and very small reaction vessels. The handling of small volumes made possible with the membrane technique described by the invention brings great savings in reagent costs.

In the device for transfer described by the invention, the contact between the magnet and protective membrane is tight. This is important when wishing to ascertain the reproducibility and strength of the magnetic field obtained by a small magnet. Especially in the case presented by the invention where the protective membrane is thin and extendable an ideal situation is realised when working with small fluid volumes and reaction vessels. Should the magnet be surrounded by a fixed, non-extendable protective hood, the contact with the magnet could not be made reproducible and tight. At the same time, the magnet with a protective hood would have a diameter considerably larger than the device for transfer described by the invention. Should the magnet be devoid of any protective membrane or coating, this would be conceived as a very unpractical solution and at great risk for contamination.

As examples of applications according to the invention the following may be mentioned:

1. Cloning of DNA Inserts

Restriction Enzymes

Creating blunt ends (e.g. thermostable polymerases, Klenow fragment DNA Polymerase I, Mung Bean nuclease)

Ligation (e.g. T4 DNA Ligase, *E. coli* DNA Ligase, T4 RNA Ligase)

Phosphorylation (e.g. T4 Polynucleotide Kinase)

Dephosphorylation (e.g. CIP, *E. coli* Alkaline Phosphatase, T4 Polynucleotide kinase)

Nested deletions (e.g. T4 DNA Polymerase, Thermostable Polymerases, Exo III Nuclease, Mung Bean nuclease).

2. Synthesising and Cloning of cDNA

E.g. Reverse Transcriptase, RNase H, DNA polymerase I, T4 DNA polymerase I, *E. coli* DNA Ligase.

3. Labelling Nucleic Acids

5' labelling (e.g. T4 Polynucleotide Kinase)

3' addition (e.g. T4 RNA Ligase)

3' fill-in (e.g. Klenow Fragment DNA Polymerase I, T4 DNA Polymerase)

3' exchange (e.g. T4 DNA Polymerase, thermostable polymerases)

Nick-translation (e.g. *E. coli* DNA Polymerase I, thermostable polymerases)

Replacement synthesis (e.g. T4 DNA Polymerase, thermostable polymerases, Exo III Nuclease)

Random priming (e.g. Klenow Fragment DNA Polymerase I, thermostable polymerases)

RNA probes (e.g. T7 RNA Polymerase, SP6 RNA Polymerase).

4. Sequencing Nucleic Acids

Sequencing DNA (e.g. *E. coli* DNA Polymerase I, Klenow Fragment DNA Polymerase I, thermostable polymerases)

Sequencing RNA (e.g. Reverse Transcriptase, thermostable reverse transcriptases).

5. Mutating Nucleic Acids

Oligonucleotide directed (e.g. T4 DNA Polymerase, T7 DNA Polymerase, thermostable polymerases)

Misincorporation (e.g. Exo III Nuclease, Klenow Fragment DNA Polymerase I, thermostable polymerases).
6. Mapping
Restriction (e.g. Exo III Nuclease)
Footprinting (e.g. Exo III Nuclease)
Transcript (e.g. Reverse Transcriptase, Mung Bean Nuclease).
7. Purifying and Isolating Nucleic Acids
Purifying plasmid DNA
Purifying PCR products
Purifying DNA probes
Purifying mRNA
Purifying DNA on agarose gel
8. Assay Methods in Molecular Biology
Molecular analysis of point mutations
DNA amplification methods [PCR, Inverse PCR, Ligase chain reaction (LCR)]
Quantification of DNA/RNA)
Ribonuclease Protection Assay
RFLP (Restriction Fragment Length Polymorphism)
9. Analytical Methods
Drug analysis [screening combinatory libraries, high throughput screening HTS)]
Food analysis (pathogens, drugs, toxins)
Environmental analysis (pesticides, herbicides, insecticides)
Diagnostics (bacteria, parasites, viruses, antibodies, antigens).
10. Cell Separation
Human leukocyte isolation
Human T-cell isolation
Cancer cell isolation.
11. Protein Purification
Affinity purification (His-tag, streptavidine-biotin, antibodies)

The embodiments of the invention mentioned above are merely suggestions for carrying out the concept of the invention. To a person skilled in the art it is clear that the diverse embodiments of the invention may vary in the scope of the claims presented hereafter.

12. Examples of Applying the Invention

In the examples presented next use is made of the device for transfer of magnetic particles according to the invention.

EXAMPLE 1

DNA Purification from Agarose Gel Using Silica Coated Paramagnetic Particles

DNA purification described below was done using the device for transfer of magnetic particles according to the invention and Merck's Silica Paramagnetic Particles for Molecular Biology.

$\lambda$-DNA digested with HindIII, was separated by electrophoresis and the 6.6 kbp fragment was cut from the gel. The piece of gel was placed in a microcentrifuge tube to which 300 $\mu$l of buffer A (7 M NaClO$_4$, 1% Sorbit, 100 mM Tris-HCl, pH 8,0) was added. The suspension was incubated in a 50° C. water bath for 10 minutes.

The microcentrifuge tube was removed from the water bath and magnetic particles were picked up using the device for transfer according to the invention. The magnetic particles were washed with 500 $\mu$l of buffer A. Washing was repeated twice using as wash liquid 500 $\mu$l of buffer B [70% ethanol, 50 mM Tris-HCl, pH 7.2, 1 mM EDTA (ethylenediaminetetraacetic acid)]. After the last wash the particles were left to dry on the tip of the device for transfer.

The particles were suspended in 20 $\mu$l of buffer C (10 mM Tris-HCl, pH 8.0, 1 mM EDTA) and incubated 5 minutes at 50° C. The particles were picked up with the device for transfer out of the solution into which the DNA fragment had been eluted.

In order to confirm purification, the DNA fragment released from the particles was electrophoresed along with a $\lambda$-HindIII standard.

EXAMPLE 2

DNA Purification from Solution Using Carboxyl Coated Paramagnetic Particles

DNA purification described below was done using the device for transfer of magnetic particles according to the invention and PerSeptive Biosystems' BioMag® DNA Isolation Kit for PCR Products.

100 $\mu$l of 4 $\mu$g/ml plasmid pUC19 solution was pipetted in a microcentrifuge tube. A 10 $\mu$l volume of washed DNA Sep particles was added thereto along with 110 $\mu$l of hybridisation buffer (20% polyethyleneglycol 8000; 2.5 M NaCl). The suspension was mixed and then incubated at room temperature for 10 minutes.

The magnetic particles were picked up out of the solution with the device for transfer according to the invention. The particles were washed twice with 100 $\mu$l of Wash Solution (70% ethanol) whereafter they were left to dry on the tip of device for transfer.

DNA was eluted from the particles by adding 30 $\mu$l of elution buffer (10 mM Tris, pH 8) and incubating for 5 minutes at room temperature. The particles were picked up out of the DNA containing solution by using the device for transfer.

In order to confirm purification, the purified pUC19 DNA released from the particles was electrophoresed along with pUC19 and $\lambda$-HindIII standards.

EXAMPLE 3

Plasmid DNA Purification from *Escherichia coil* Bacterial Cells Using Carboxyl Coated Paramagnetic Particles DNA purification described below was done using the device for transfer of magnetic particles according to the invention and PerSeptive Biosystems' BioMag® Mini-Prep DNA Purification Kit. The 9.0 kbp plasmid to be isolated was transformed in *E. coli* cells.

3 ml of bacterial cell culture was centrifuged and the supernatant discarded. The pellet of cells was suspended in 30 $\mu$l of Solution 1 (50 mM glucose, 25 mM Tris, 10 mM EDTA). 10 $\mu$l of RNase and 60 $\mu$l of Solution 2 (0,2 M NaOH, 1% SDS) were added. The suspension was incubated at room temperature for 5 minutes. 45 $\mu$l of Solution 3 was added (3 M potassium, 5 M acetate) and the suspension was incubated on ice for 10 minutes. The mixture was centrifuged for 10 min at 15 800×g.

The supernatant was transferred to a microcentrifuge tube containing 10 $\mu$l of washed DNA Sep particles. 150 $\mu$l of 2× Hybridization Solution (20% polyethylene glycol 8000; 2.5 M NaCl) was added, and reaction mixture was incubated at room temperature for 10 minutes.

Magnetic particles were picked up out of the solution using the device for transfer according to the invention. The particles were washed twice with 200 $\mu$l of Wash Solution (70% ethanol) whereafter they were left to dry on the tip of the device for transfer.

DNA was eluted from the particles by adding 30 $\mu$l of Elution Solution (10 mM Tris, pH 8) and incubating for 5 min at room temperature. The particles were picked up out of the DNA containing solution with the device for transfer.

In order to confirm purification, the purified plasmid DNA released from the particles was electrophoresed along with $\lambda$-HindIII standards.

EXAMPLE 4
DNA Digestion Using Restricaon Enzyme Immobilised on Magnetic Particles 25 μg of restriction enzyme BglII and 1.3 mg of washed Dynal's Dynabeads® M-280 Tosylactivated Superparamagnetic Particles were suspended in 160 μl of 0.1 M borate buffer, pH 9.5. The suspension was incubated for 7 days at 8° C. with gentle mixing.

The magnetic particles were picked up out of the solution with the device for transfer according to the invention and washed twice at 4° C. for 5 min each time with PBS buffer [phosphate buffered saline that contains 0.1% (w/v) BSA (Bovine Serum Albumin)]. The particles were washed once at 8° C. for 2 days in 0.2 M Tris buffer (pH 8.5; 0.1% BSA) and once at 4° C. for 5 min with PBS buffer. The washed particles were suspended in 160 μl of PBS buffer.

1 μg of λ-DNA in 50 μl of 6 mM Tris buffer [pH 7.9; 150 mM NaCl; 6 mM $MgCl_2$; 1 mM DTT (dithiothreitol)] was digested at 37° C. for 1 h using different amounts of restriction enzyme BglII immobilised on magnetic particles. After digestion magnetic particles were picked up out of the solution with the device for transfer according to the invention.

In order to confirm purification, the digested DNA was electrophoresed along with λ-HindIII standard and soluble BglII digested λ-DNA.

EXAMPLE 5
Dephosphorylation of DNA Fragments Using CIP Immobilised on Magnetic Particles 10 mg of washed Prolabo's Estapor EM2 100/40 Superparamagnetic Particles was suspended in 900 μl of 20 mM phosphate buffer (pH 7.4; 150 mM NaCl; 1 mM $MgCl_2$; 0.1 mM $ZnCl_2$). 2 mg of DSS (disuccinateimidyl suberate) suspended in 100 μl of DMF (N,N-dimethyl formamide) was added to the suspension. The suspension was incubated at room temperature for 15 min slowly mixing.

Magnetic particles were picked up out of the solution with the device for transfer according to the invention and washed once with 1 ml and once with 0.5 ml of phosphate buffer at room temperature.

The particles were suspended in 200 μl of phosphate buffer that contained 160 μg of CIP (Calf Intestinal Phosphatase) and the suspension was incubated for 30 min in room temperature slowly mixing.

Magnetic particles were picked up out of the solution with the device for transfer and washed twice with 0.5 ml of phosphate buffer at room temperature. The particles were suspended in 1 ml of 35 mM Tris buffer(pH 8.0; 50 mM KCl; 1 mM $MgCl_2$; 0.1 M $ZnCl_2$) and incubated at room temperature for 30 minutes slowly mixing.

Magnetic particles were picked up out of the solution with the device for transfer and washed twice with 1 ml of 10 mM Tris buffer (pH 8.0; 50 mM KCl; 1 mM $MgCl_2$; 0.1 $ZnCl_2$) at room temperature. The particles were resuspended in 1 ml of the same buffer.

Plasmid pUC19 DNA was cut with soluble restriction enzyme BglII to get 1 568 bp and 1 118 bp fragments. 0.5 μg of the fragments were incubated for 1 h at 3° C. with different amounts of CIP bound to magnetic particles. 10 μl of 10 mM Tris (pH 7.9; 10 mM $MgCl_2$; 1 mM DTT; 50 mM NaCl) was used as reaction buffer.

After dephosphorylation the particles with CIP immobilised thereon were picked up out of the reaction mixture with the device for transfer according to invention.

7.5 μl of $H_2O$, 2 μl of 300 mM Tris (pH 7.8; 100 mM $MgCl_2$; 100 mM DTT; 10 mM ATP) and 0.5 μl of ligase (3 U/μl) were added to the dephosphorylated fragments and the reaction mixture thus obtained was incubated at 15° C. for 17 h.

The ligase treated DNA fragments were electrophoresed along with λ-HindIII standard, ligation controls and uncut pUC19 plasmid in order to confirm the functionality of CIP immobilised on magnetic particles.

EXAMPLE 6
Restriction Enzyme Inactivation Using Proteinase K Immobilised on Magnetic Particles 0.23 mg of B-9-ITC (biotin isocyanate with a nine atom spacer) was dissolved in 50 μl of DMF (N,N-dimethyl formamide). To this was added 0.45 mg of proteinase K to be biotinylated dissolved in 450 μl of 50 mM borate buffer, pH 9.5. The suspension was incubated at room temperature for 3.5 h slowly mixing. Any biotinylation reagent left unreacted was removed from the solution by gel filtration. At the same time, the buffer was changed to PBS (phosphate buffered saline, pH 7.4). Half of the biotinylated and gel filtered proteinase K was used for immobilisation.

10 mg of washed Merck's BioBeads Streptavidin Paramagnetic Particles was suspended in 1 ml of gel filtered proteinase K solution. The suspension was incubated at room temperature for 30 minutes slowly mixing.

The magnetic particles were picked up out of the solution with the device for transfer according to the invention and washed twice with 1 ml of 10 mM $Na_2HPO_4$, pH 7.4, 150 mM NaCl solution at room temperature and eight times with 1 ml of 6 mM Tris buffer (pH 7.5; 6 mM $MgCl_2$; 100 mM NaCl; 1 mM DTT) at 50° C. for 30 minutes. The washed particles were suspended in 1 ml of Tris buffer (pH 8.0; 10 mM $CaCl_2$).

Varying amounts of proteinase K imnnobilised on magnetic particles were suspended in 35 μl of reaction solution containing 35 U of restriction enzyme BglII in 6 mM Tris buffer (pH 7.5; 6 mM $MgCl_2$; 100 mM NaCl; 1 mM DTT) and the suspension was incubated for 1 h at 37° C.

After inactivation of the restriction enzyme the magnetic particles were picked up out of the solution using the device for transfer according to the invention. Inactivation with magnetic particle bound proteinase K of restriction enzymes BamHI and HindIII was also performed as above for BglII but using as reaction buffer 6 mM Tris buffer (pH 7.9; 6 mM $MgCl_2$; 150 mM NaCl; 1 mM DTT).

Restriction enzyme activity after inactivation was assayed using λ-DNA as substrate. Restriction enzyme inactivation was confirmed electrophoretically by isolating samples along with digested DNA standard.

EXAMPLE 7
Detection of Polyaromatic Hydrocarbons Using a Magnetic Particle Based Immunoassay Detection of polyaromatic hydrocarbons (PAH) was carried out with the device for transfer according to the invention and Strategic Diagnostics' PAHs RaPID Assay® which is an enzyme linked magnetic, particle based immunoassay.

150 μl of 2, 10 and 50 ppb phenanthrene standards were pipetted in microcentrifuge tubes in duplicate. 150 μl of PAHs Antibody Enzyme Conjugate (PAH analogue labelled with horseradish peroxidase) and 300 μl of PAHs Antibody Coupled Paramagnetic Particles (rabbit anti-PAH antibodies bound covalently to microparticles) were added to the tubes. Reaction mixtures were incubated at room temperature for 30 minutes.

The magnetic particles were picked up out of reaction solutions with the device for transfer according to the invention and washed twice with 600 μl of Washing Solution (water plus detergent).

The particles were suspended in 300 μl of Color Solution (hydrogen peroxide and 3,3',5,5'-tetramethyl bentsidine in an organic base) and incubated at room temperature for 20 minutes. 500 µl of Stopping Solution (0.5% sulphuric acid) was added to each tube.

Samples were measured spectrophotometrically at 450 nm using Washing Solution as a blank. A standard curve was plotted of the results.

What is claimed is:

1. A transfer device for capturing and releasing microparticles, comprising
   a magnet having a magnetic field for capturing microparticles,
   an extendible membrane having a first side and a second side, and
   means for joining and separating said magnet and said first side of said membrane, such that in operation said magnet is releasably pressed against said first side of said membrane, thereby stretching said membrane, to enable microparticles to be fixed by magnetic attraction to said second side of said membrane, until said magnet is separated from said first side of said membrane, thereby releasing said microparticles from said second side of said membrane.

2. The transfer device of claim 1, wherein said magnet is a permanent magnet axially moveable back and forth within a tubular body part, and wherein said membrane is located on one end of said tubular body part such that said magnet can be pressed against said first side of said membrane to stretch said membrane.

3. The transfer device of claim 2, wherein said tubular body part is operably connected to a pipette having a body and a device for controlling operation of said pipette, such that movement of said magnet within said tubular body part may be controlled by said controlling device.

4. The transfer device of claim 1, wherein the magnet is made of magnetizable material which is magnetized with an electric field or with the aid of a permanent magnet.

5. The transfer device of claim 1, further comprising at least one additional magnet to enable transfer of a substance immobilized on said microparticles from at least two first neighboring vessels to at least two second neighboring vessels.

6. The transfer device of claim 5, wherein said membrane is common to at least two magnets.

7. The transfer device of claim 6, further comprising sleeves in which said magnets move in axial direction and by which said membrane is stretched.

8. The transfer device of claim 6, wherein said membrane has a preshaped area to receive said magnet.

9. The transfer device of claim 1, wherein said means for joining and separating said magnet and said first side of said extendible meirbrane comprise two essentially parallel first and second elongated arms, such that said magnet is located on a first end of said first elongated arm and said membrane is located on a first end of said second elongated arm.

10. The transfer device of claim 9, wherein said extendible membrane forms a base of a nose piece releasably attached to said second elongated arm.

11. The transfer device of claim 9, wherein said elongated arms are connected to one another, and the arms are optionally subjected to a spring force that strives to bring the first ends of the arms either further apart or closer together.

12. The transfer device of claim 1, wherein said extendible membrane is made of silicone rubber.

13. A method for transferring a substance immobilized to microparticles from a first vessel to a second vessel, wherein the microparticles are of magnetic or magnetizable material or the microparticles are attached to a magnetic or magnetizable body, comprising stretching an extendible membrane by releasably pressing a magnet against a first side of said membrane,
capturing said microparticles on a second side of said membrane by submerging said magnet in said first vessel containing said microparticles, such that the membrane pressed against the magnet's surface separates the magnet from the microparticles but does not substantially weaken the magnetic field directed at the microparticles,
transferring the magnet along with the microparticles captured thereupon to the second vessel, and
releasing the microparticles from said second side of said membrane by withdrawing said magnet from said membrane.

14. The method of claim 13, wherein the magnet is a permanent magnet.

15. The method of claim 13, wherein the magnet is made of magnetizable material which is magnetized with an electric field or with the aid of a permanent magnet.

16. The method of claim 13, wherein the microparticles are selected from the group consisting of paramagnetic, superparamagnetic and ferromagnetic particles.

17. The method of claim 13, wherein the immobilized substance is a member selected from the group consisting of a protein, a polypeptide and a hapten.

18. The method of claim 17, wherein said protein is selected from the group consisting of a restriction enzyme, a DNA modifying enzyme and a RNA modifying enzyme.

19. The method of claim 17, wherein the protein is a protease.

20. The method of claim 19, wherein said protease is proteinase K.

21. The method of claim 13, wherein the immobilized substance is a nucleic acid.

22. The method of claim 13, wherein the immobilized substance is a cell or a virus.

23. The method of claim 13, wherein the substance immobilized on magnetic or magnetizable microparticles is transferred using a transfer device attached to automated equipment.

24. A method for modifying nucleic acid with a nucleic acid modifying enzyme, comprising transferring the enzyme immobilized on microparticles into a reaction vessel where the modification of the nucleic acid is to take place, and
removing the immobilized enzyme from the reaction vessel by a method comprising
    stretching an extendible membrane by releasably pressing a magnet against a first side of said membrane,
    capturing said microparticles on a second side of said membrane by submerging said magnet in a first vessel containing said microparticles, such that the membrane pressed against the magnet's surface separates the magnet from the microparticles but does not substantially weaken the magnetic field directed at the microparticles,
    transferring the magnet along with the microparticles captured thereupon to the second vessel, and
    releasing the microparticles from said second side of said membrane by withdrawing said magnet from said membrane.

25. A method for transferring nucleic acid from one vessel to another, comprising transferring microparticles, on which the nucleic acid is to be bound, into a reaction vessel wherein the nucleic acid is bound to the microparticles, and removing the microparticles from the reaction vessel by a method comprising stretching an extendible membrane by releasably pressing a magnet against a first side of said membrane, capturing said microparticles on a second side of said membrane by submerging said magnet in a first vessel containing said microparticles, such that the membrane pressed against the magnet's surface separates the magnet from the microparticles but does not substantially weaken the magnetic field directed at the microparticles, transferring the magnet along with the microparticles captured thereupon to the second vessel, and releasing the microparticles from said second side of said membrane by withdrawing said magnet from said membrane.

26. A sample processing system, comprising:

at least one series of wells which comprises at least a first well adapted to contain an amount of microparticles to be dosed and optionally at least one preservative, and optionally a second well adapted to contain a second substance in which said amount of microparticies are submerged for a first treatment before being optionally introduced to a third well where a second treatment can occur, and a transfer device that comprises a magnet in combination with an extendible membrane and means for joining and separating said magnet and said extendible membrane, such that in operation the magnet is releasably pressed against one side of the membrane to stretch said membrane, such that the membrane pressed against the magnet separates the magnet from the microparticles but does not substantially weaken the magnetic field directed at the microparticies.

27. The sample processing system of claim 26, wherein each series of wells forms a separate strip and that a desired number of strips, that may optionally be interconnected, form a plate.

* * * * *